US012681996B2

(12) United States Patent
Nouira

(10) Patent No.: US 12,681,996 B2
(45) Date of Patent: Jul. 14, 2026

(54) SYSTEMS AND METHODS FOR BUILDING AN ELECTRONIC DATA CAPTURE SYSTEM

(71) Applicant: MEDIDATA SOLUTIONS, INC., New York, NY (US)

(72) Inventor: Marouane Nouira, Cincinnati, OH (US)

(73) Assignee: MEDIDATA SOLUTIONS, INC., New York, NY (US)

( * ) Notice: Subject to any disclaimer, the term of this patent is extended or adjusted under 35 U.S.C. 154(b) by 348 days.

(21) Appl. No.: 18/472,910

(22) Filed: Sep. 22, 2023

(65) Prior Publication Data

US 2025/0103660 A1 Mar. 27, 2025

(51) Int. Cl.
*G06F 16/93* (2019.01)
*G06F 16/16* (2019.01)
*G06F 40/30* (2020.01)
*G16H 10/20* (2018.01)

(52) U.S. Cl.
CPC .............. *G06F 16/93* (2019.01); *G06F 16/16* (2019.01); *G06F 40/30* (2020.01); *G16H 10/20* (2018.01)

(58) Field of Classification Search
CPC ....................................................... G06F 16/93
See application file for complete search history.

(56) References Cited

U.S. PATENT DOCUMENTS

| | | | |
|---|---|---|---|
| 2017/0061103 A1* | 3/2017 | Bain et al. ............ | G06F 19/363 |
| 2022/0351810 A1 | 11/2022 | Mohan et al. | |
| 2023/0176829 A1* | 6/2023 | Rahmani et al. ......... | G06F 8/33 |
| 2024/0176803 A1* | 5/2024 | Gupta et al. .......... | G06F 16/285 |

FOREIGN PATENT DOCUMENTS

| | | | |
|---|---|---|---|
| JP | 2015-153137 A | 8/2015 | |
| WO | WO 2015/126457 A1 * | 8/2015 | ............. G06Q 10/00 |

OTHER PUBLICATIONS

Aliveforms, "How to create survey using ChatGPT", Jul. 15, 2023, https://www.youtube.com/watch?v=bJfQtjk_Gok, retrieved on Feb. 6, 2025, 2 pages.
Superbsic et al., "Fine-tuning (deep learning)", Wikipedia, Aug. 5, 2023, https://en.wikipedia.org/w/index.php?title=Fine-tuning_(deep_learning)&oldid=1168828327, retrieved on Feb. 6, 2025, pp. 1-4.
Extended European Search Report from European Patent Application No. 24201052.8, Feb. 27, 2025, 9 pages.
1 Decision to Grant from Japanese Patent Application No. 2024-145051, Nov. 11, 2025, 5 pages.

* cited by examiner

*Primary Examiner* — James J Debrow

(74) *Attorney, Agent, or Firm* — STEPTOE LLP; Carl B. Wischhusen

(57) ABSTRACT

Disclosed are methods and systems for building an electronic data capture (EDC) system. The method includes forming a training dataset from a set of protocol documents and corresponding EDC builds. The method includes using the set of protocol documents and corresponding EDC builds of the training dataset to fine tune a pre-trained language model to produce an EDC build model. The method includes inputting a protocol document to the EDC build model to produce an EDC build prediction. The method includes generating data structures of the EDC system based at least in part on the EDC build prediction.

24 Claims, 18 Drawing Sheets

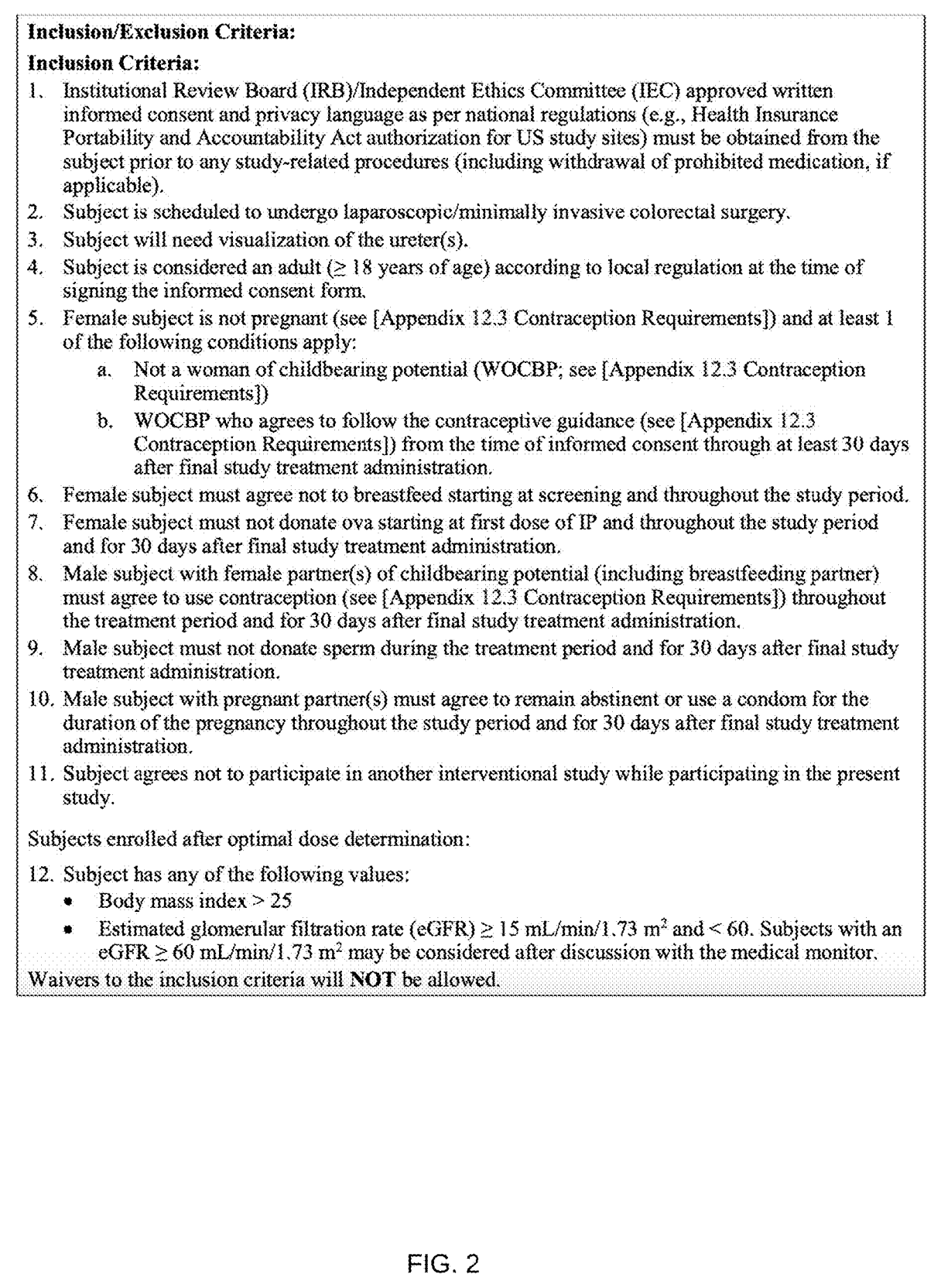

Inclusion/Exclusion Criteria:

Inclusion Criteria:

1. Institutional Review Board (IRB)/Independent Ethics Committee (IEC) approved written informed consent and privacy language as per national regulations (e.g., Health Insurance Portability and Accountability Act authorization for US study sites) must be obtained from the subject prior to any study-related procedures (including withdrawal of prohibited medication, if applicable).

2. Subject is scheduled to undergo laparoscopic/minimally invasive colorectal surgery.

3. Subject will need visualization of the ureter(s).

4. Subject is considered an adult ($\geq$ 18 years of age) according to local regulation at the time of signing the informed consent form.

5. Female subject is not pregnant (see [Appendix 12.3 Contraception Requirements]) and at least 1 of the following conditions apply:

a. Not a woman of childbearing potential (WOCBP; see [Appendix 12.3 Contraception Requirements])

b. WOCBP who agrees to follow the contraceptive guidance (see [Appendix 12.3 Contraception Requirements]) from the time of informed consent through at least 30 days after final study treatment administration.

6. Female subject must agree not to breastfeed starting at screening and throughout the study period.

7. Female subject must not donate ova starting at first dose of IP and throughout the study period and for 30 days after final study treatment administration.

8. Male subject with female partner(s) of childbearing potential (including breastfeeding partner) must agree to use contraception (see [Appendix 12.3 Contraception Requirements]) throughout the treatment period and for 30 days after final study treatment administration.

9. Male subject must not donate sperm during the treatment period and for 30 days after final study treatment administration.

10. Male subject with pregnant partner(s) must agree to remain abstinent or use a condom for the duration of the pregnancy throughout the study period and for 30 days after final study treatment administration.

11. Subject agrees not to participate in another interventional study while participating in the present study.

Subjects enrolled after optimal dose determination:

12. Subject has any of the following values:
    - Body mass index > 25
    - Estimated glomerular filtration rate (eGFR) $\geq$ 15 mL/min/1.73 m$^2$ and < 60. Subjects with an eGFR $\geq$ 60 mL/min/1.73 m$^2$ may be considered after discussion with the medical monitor.

Waivers to the inclusion criteria will NOT be allowed.

FIG. 2

```
<Row ss:AutoFitHeight="1">
<Cell ss:StyleID="Protected"><Data ss:Type="String">IE_1</Data></Cell>
<Cell ss:StyleID="Protected"><Data ss:Type="String">IEYN</Data></Cell>
<Cell ss:StyleID="Default"><Data ss:Type="String">47</Data></Cell>
<Cell ss:StyleID="Default" ss:Index="5"><Data ss:Type="String">IEYN</Data></Cell>
<Cell ss:StyleID="Default"><Data ss:Type="String">TRUE</Data></Cell>
<Cell ss:StyleID="Protected"><Data ss:Type="String">IEYN</Data></Cell>
<Cell ss:StyleID="Default"><Data ss:Type="String">1</Data></Cell>
<Cell ss:StyleID="Default"><Data ss:Type="String">NY</Data></Cell>
<Cell ss:StyleID="Default" ss:Index="12"><Data ss:Type="String">RadioButton (Vertical)</Data></Cell>
<Cell ss:StyleID="Default" ss:Index="14"><Data ss:Type="String">0</Data></Cell>
<Cell ss:StyleID="Default" ss:Index="19"><Data ss:Type="String">Is the subject fully eligible per the Inclusion Criteria?</Data></Cell>
<Cell ss:StyleID="Default"><Data ss:Type="String">FALSE</Data></Cell>
<Cell ss:StyleID="Default" ss:Index="22"><Data ss:Type="String">Eligible Per Criteria</Data></Cell>
<Cell ss:StyleID="Default" ss:Index="25"><Data ss:Type="String">FALSE</Data></Cell>
<Cell ss:StyleID="Default"><Data ss:Type="String">FALSE</Data></Cell>
<Cell ss:StyleID="Default"><Data ss:Type="String">TRUE</Data></Cell>
<Cell ss:StyleID="Default" ss:Index="30"><Data ss:Type="String">FALSE</Data></Cell>
<Cell ss:StyleID="Default"><Data ss:Type="String">FALSE</Data></Cell>
<Cell ss:StyleID="Default"><Data ss:Type="String">FALSE</Data></Cell>
<Cell ss:StyleID="Default"><Data ss:Type="String">FALSE</Data></Cell>
<Cell ss:StyleID="Default"><Data ss:Type="String">FALSE</Data></Cell>
<Cell ss:StyleID="Default"><Data ss:Type="String">FALSE</Data></Cell>
<Cell ss:StyleID="Default"><Data ss:Type="String">FALSE</Data></Cell>
<Cell ss:StyleID="Default"><Data ss:Type="String">FALSE</Data></Cell>
<Cell ss:StyleID="Default" ss:Index="44"><Data ss:Type="String">Data Management Review</Data></Cell>
<Cell ss:StyleID="Default"><Data ss:Type="String">FALSE</Data></Cell>
<Cell ss:StyleID="Default"><Data ss:Type="String">1062114</Data></Cell>
<Cell ss:StyleID="Default"><Data ss:Type="String">687733</Data></Cell>
<Cell ss:StyleID="Default"><Data ss:Type="String">550608</Data></Cell>
<Cell ss:StyleID="Default"><Data ss:Type="String">351763</Data></Cell>
<Cell ss:StyleID="Protected" ss:Index="52"><Data ss:Type="String">AFP</Data></Cell>
<Cell ss:StyleID="Default" ss:Index="200" ss:Formula="=IF(LEN(UnitDictionaries!RC1)>0,UnitDictionaries!RC1,"")"/>
<Cell ss:StyleID="Default" ss:Index="201" ss:Formula="=IF(LEN(Forms!RC1)>0,Forms!RC1,"")"/>
<Cell ss:StyleID="Default" ss:Index="202" ss:Formula="=IF(LEN(DataDictionaries!RC1)>0,DataDictionaries!RC1,"")"/>
</Row>
```

```
<Row ss:AutoFitHeight="1">
<Cell ss:StyleID="Default"><Data ss:Type="String">IETESTI</Data></Cell>
<Cell ss:StyleID="Default"><Data ss:Type="String">IN01</Data></Cell>
<Cell ss:StyleID="Default"><Data ss:Type="String">1</Data></Cell>
<Cell ss:StyleID="Default"><Data ss:Type="String">1. Institutional Review Board (IRB)/Independent Ethics Committee (IEC) approved
written informed consent and privacy language as per national regulations (e.g., Health Insurance Portability and Accountability Act
authorization for US study sites) must be obtained from the subject prior to any study-related procedures (including withdrawal of
prohibited medication, if applicable).</Data></Cell>
<Cell ss:StyleID="Default"><Data ss:Type="String">FALSE</Data></Cell>
<Cell ss:StyleID="Default" ss:Index="200" ss:Formula="=IF(LEN(DataDictionaries!RC1)>0,DataDictionaries!RC1,"")"/>
</Row>
<Row ss:AutoFitHeight="1">
<Cell ss:StyleID="Default"><Data ss:Type="String">IETESTI</Data></Cell>
<Cell ss:StyleID="Default"><Data ss:Type="String">IN02</Data></Cell>
<Cell ss:StyleID="Default"><Data ss:Type="String">2</Data></Cell>
<Cell ss:StyleID="Default"><Data ss:Type="String">2. Subject is scheduled to undergo laparoscopic/minimally invasive colorectal
surgery.</Data></Cell>
<Cell ss:StyleID="Default"><Data ss:Type="String">FALSE</Data></Cell>
<Cell ss:StyleID="Default" ss:Index="200" ss:Formula="=IF(LEN(DataDictionaries!RC1)>0,DataDictionaries!RC1,"")"/>
</Row>
<Row ss:AutoFitHeight="1">
<Cell ss:StyleID="Default"><Data ss:Type="String">IETESTI</Data></Cell>
<Cell ss:StyleID="Default"><Data ss:Type="String">IN03</Data></Cell>
<Cell ss:StyleID="Default"><Data ss:Type="String">6</Data></Cell>
<Cell ss:StyleID="Default"><Data ss:Type="String">3. Subject will need visualization of the ureter(s).</Data></Cell>
<Cell ss:StyleID="Default"><Data ss:Type="String">FALSE</Data></Cell>
<Cell ss:StyleID="Default" ss:Index="200" ss:Formula="=IF(LEN(DataDictionaries!RC1)>0,DataDictionaries!RC1,"")"/>
</Row>
<Row ss:AutoFitHeight="1">
<Cell ss:StyleID="Default"><Data ss:Type="String">IETESTI</Data></Cell>
<Cell ss:StyleID="Default"><Data ss:Type="String">IN04</Data></Cell>
<Cell ss:StyleID="Default"><Data ss:Type="String">8</Data></Cell>
<Cell ss:StyleID="Default"><Data ss:Type="String">4. Subject is considered an adult (>= 18 years of age) according to local
regulation at the time of signing the informed consent form (ICF).</Data></Cell>
<Cell ss:StyleID="Default"><Data ss:Type="String">FALSE</Data></Cell>
<Cell ss:StyleID="Default" ss:Index="200" ss:Formula="=IF(LEN(DataDictionaries!RC1)>0,DataDictionaries!RC1,"")"/>
</Row>
<Row ss:AutoFitHeight="1">
<Cell ss:StyleID="Default"><Data ss:Type="String">IETESTI</Data></Cell>
<Cell ss:StyleID="Default"><Data ss:Type="String">IN05</Data></Cell>
<Cell ss:StyleID="Default"><Data ss:Type="String">10</Data></Cell>
<Cell ss:StyleID="Default"><Data ss:Type="String">5. Female subject is not pregnant (see [Appendix 12.3 Contraception Requirements]
and at least 1 of the following conditions apply: a. Not a woman of childbearing potential (WOCBP; see [Appendix 12.3 Contraception
Requirements]); b. WOCBP who agrees to follow the contraceptive guidance (see [Appendix 12.3 Contraception Requirements] from the time
of informed consent through at least 30 days after final study treatment administration.</Data></Cell>
<Cell ss:StyleID="Default"><Data ss:Type="String">FALSE</Data></Cell>
<Cell ss:StyleID="Default" ss:Index="200" ss:Formula="=IF(LEN(DataDictionaries!RC1)>0,DataDictionaries!RC1,"")"/>
</Row>
```

| | A | B | C | D | E |
|---|---|---|---|---|---|
| | DataDictionaryName | CodedData | Ordinal | UserDataString | Specify |
| 87 | IETESTI | IN02 | 2 | 2. Subject is scheduled to undergo laparoscopic/minimally invasive colorectal surgery. | FALSE |
| 88 | IETESTI | IN03 | 3 | 3. Subject will need visualization of the ureter(s). | FALSE |
| 89 | IETESTI | IN04 | 8 | 4. Subject is considered an adult (>= 18 years of age) according to local regulation at the time of signing the informed consent form (ICF). 5. Female subject is not pregnant (see [Appendix 12.3 Contraception Requirements]) and at least 1 of the following conditions apply: a. Not a woman of childbearing potential (WOCBP; see [Appendix 12.3 Contraception Requirements]); b. WOCBP who agrees to follow the contraceptive guidance (see [Appendix 12.3 Contraception Requirements]) from the time of informed consent through at least 30 days after final study treatment administration. | FALSE |
| 90 | IETESTI | IN05 | 10 | 6. Female subject must agree not to breastfeed starting at screening and throughout the study period. | FALSE |
| 91 | IETESTI | IN06 | 11 | | FALSE |

FIG. 6

Figure 7:
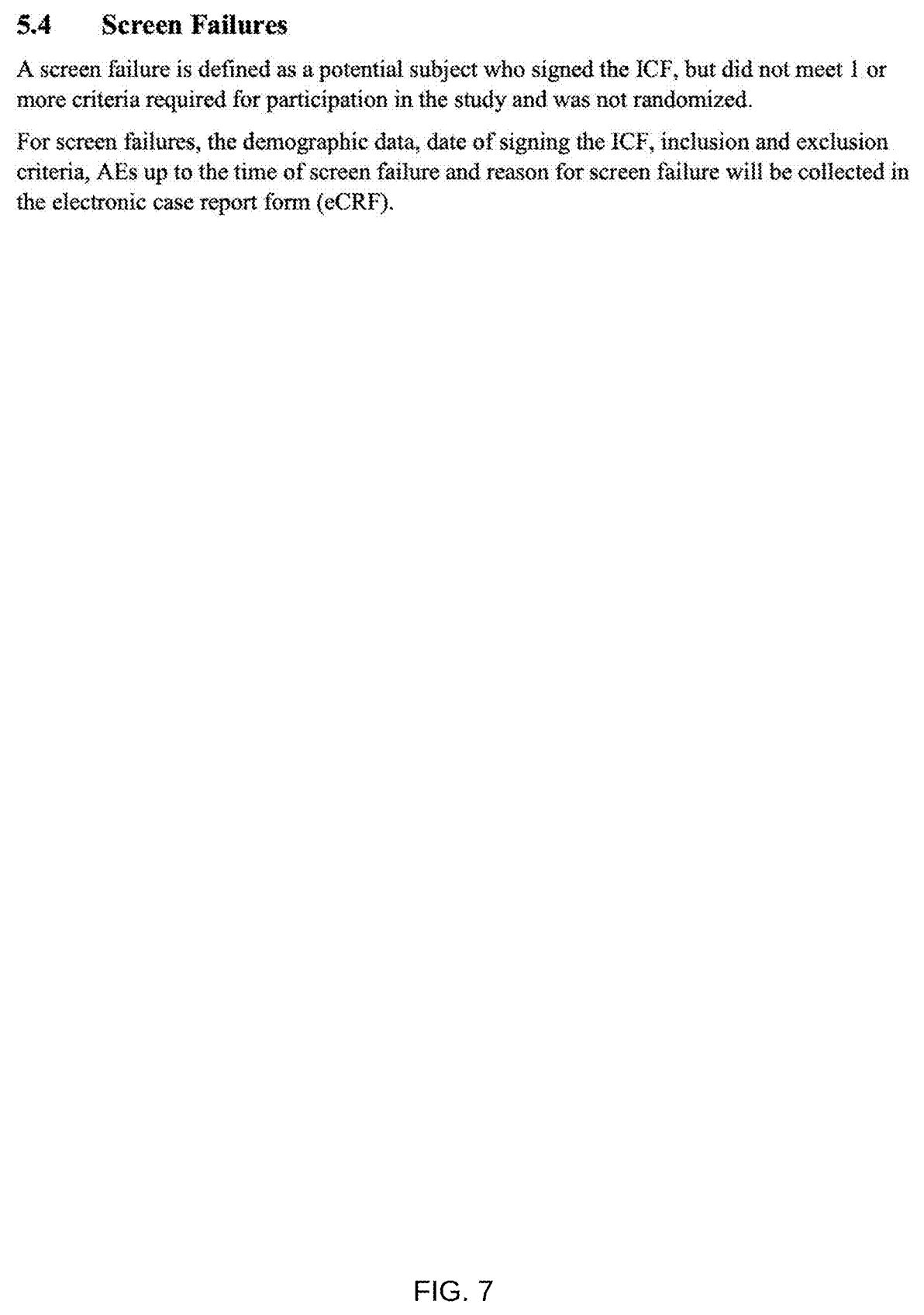

5.4     Screen Failures

A screen failure is defined as a potential subject who signed the ICF, but did not meet 1 or more criteria required for participation in the study and was not randomized.

For screen failures, the demographic data, date of signing the ICF, inclusion and exclusion criteria, AEs up to the time of screen failure and reason for screen failure will be collected in the electronic case report form (eCRF).

```
<Row ss:AutoFitHeight="1">
<Cell ss:StyleID="Protected"><Data ss:Type="String">CF_SUBJECT_STATUS</Data></Cell>
<Cell ss:StyleID="Default"><Data ss:Type="String">/*sirisha mareddy :09JAN2019 (CF_Subject_Status)
          //If any of the
forms among these are inactivate then subject status will not get updated but need one other form to update status*/

// Pavan Kumar Kanchi: 11 Aug 21, Updated Code as per Study requirement.
         ActionFunctionParams afp =
(ActionFunctionParams)ThisObject;
         DataPoint dp = afp.ActionDataPoint;
          DataPage dpg =
dp.Record.DataPage;
         Subject subject = dp.Record.Subject;

    // Pull ID of the subject
statuses
         int statusid1 = SubjectStatus.FindByName("Screening").ID;
        int statusiD2 =
SubjectStatus.FindByName("Screen Failed").ID;
        int statusiD3 =
SubjectStatus.FindByName("Run-In").ID;
          int statusiD4 = SubjectStatus.FindByName("Run-In Early
Terminated").ID;
         int statusiD5 = SubjectStatus.FindByName("Randomized/Registered").ID;

        int statusiD6 = SubjectStatus.FindByName("Early Terminated").ID;
         int statusiD7 =
SubjectStatus.FindByName("Follow-Up").ID;
         int statusiD8 = SubjectStatus.FindByName("Long Term
Follow-Up").ID;
          int statusiD9 = SubjectStatus.FindByName("Completed").ID;
//Screening
        DataPoints dp1 = CustomFunction.FetchAllDataPointsForOIDPath("DSDECOD", "DS_1", null, subject);//Screening
&DS_2", null, subject);//Run-In && Run-In Early Terminated
      // DataPoints dp3 =        // DataPoints dp3 =
CustomFunction.FetchAllDataPointsForOIDPath("DSDECOD", "DS_3", null, subject);///Randomized/Registered &&
Early Terminated
        DataPoints dp4 = CustomFunction.FetchAllDataPointsForOIDPath("DSDECOD",
"DS_4", null, subject);//Randomized/Registered
          DataPoints dp5 =
CustomFunction.FetchAllDataPointsForOIDPath("DSDECOD", "DS_5", null, subject);//Follow-Up

DataPoints dp6 = CustomFunction.FetchAllDataPointsForOIDPath("DSDECOD", "DS_6", null, subject);//Long Term
Follow-Up && Completed

        // Screen Failed
         
          subject.SubjectStatus = statusiD1;
if
(dp1.Count > 0 && dp1[0] != null && dp1[0].Active && dp1[0].Active && dp1[0].Data !=
string.Empty)
          {
          //Randomized/Registered
            subject.SubjectStatus =
statusiD5;
         if (dp1.Count > 0 && dp1[0] != null
&& dp1[0].Active && dp1[0].Active && dp1[0].Data != null
&& dp4[0].Active && dp4[0].Active && dp4[0] != null
dp4[0].Data == string.Empty)}  }
         //Early Terminated

&& dp4[0].Active && dp4[0].Data != "1" && dp4[0] != null &&
{
            subject.SubjectStatus = statusiD6;
        if (dp4.Count > 0 && dp4[0] != null && dp4[0].Active && dp4[0].Data ==
//Completed
            if (dp4.Count > 0 && dp4[0] != null && dp4[0].Active && dp4[0].Data ==
"1" && dp4[0] != null && dp4[0].Active && dp4[0].Data != null &&
string.Empty)
            subject.SubjectStatus =                  //Follow-Up

        }
       //Randomized/Registered
         if (dp5.Count > 0
&& dp5[0] != null && dp5[0].Active && dp5[0].Data == "1" && && dp5[0].Data != string.Empty
dp4[0].Data == string.Empty)}  }
            "1" && dp5[0].Data == statusiD7;

}
         //Long Term Follow-Up
           if (dp6.Count > 0 && dp5[0] != null
&& dp5[0].Active && dp5[0].Data == "1" && ((dp6.Count > 0 && dp6[0] != null &&
dp6[0].Active && dp6[0].Data == string.Empty) || dp6.Count == 0))
           //Follow-Up

subject.SubjectStatus = statusiD8;
           //else if
(dp4.Count > 0 && dp4[0] != null && dp4[0].Active && dp4[0].Data == "1" && dp4[0].Data !=
string.Empty && dp3.Count > 0 && dp3[0] != null && dp3[0].Active && dp3[0].Data == "1")
&& dp5[0] != null && dp5[0].Active && dp5[0].Data == "1" && dp5[0].Data != string.Empty;//

statusiD7;
            //Run-In Early Terminated
           ///else if
(dp2.Count > 0 && dp2[0] != null && dp2[0].Active && dp2[0].Data != "1" && dp2[0].Data !=
string.Empty)
           //Run-In ~ need update ~ Comment this section of Run-In status not being used in study
        //else if
           ///Run-In ~ need update ~ Comment this section of Run-In status not being used in study

(dp1.Count > 0 && dp1[0] != null && dp1[0].Active && dp1[0].Data == "1" && dp2.Count >
0) // V3 updates
            subject.SubjectStatus = statusiD3;
           //else if (dp1.Count > 0
//
         //// Screening is default, we can maybe comment it out
         //else if (dp1.Count > 0
&& dp1[0] != null && dp1[0].Active && dp1[0].Data == string.Empty)

```

| FunctionName | SourceCode | Lang |
|---|---|---|
| CF_SUBJECT_STATUS | /*gisha sharsity :09JAN2019 (CF_Subject_Status)<br>//If any of the forms among these are inactivate than subject status will not get updated but need one other form to update status */<br>// Pavan Kumar Kanchi; 11 Aug 21, Updated Code as per Study requirement.<br>ActionFunctionParams afp = (ActionFunctionParams)this.Object;<br>DataPoint dp = afp.ActionDataPoint;<br>DataPage dpg = dp.Record.DataPage;<br>Subject subject = db.Record.Subject;<br><br>// Pull ID of the subject statuses<br>int statusID1 = SubjectStatus.FindByName("Screening").ID;<br>int statusID2 = SubjectStatus.FindByName("Screen Failed").ID;<br>int statusID3 = SubjectStatus.FindByName("Run-In").ID;<br>int statusID4 = SubjectStatus.FindByName("Run-In Early Terminated").ID;<br>int statusID5 = SubjectStatus.FindByName("Randomized/Registered").ID;<br>int statusID6 = SubjectStatus.FindByName("Early Terminated").ID;<br>int statusID7 = SubjectStatus.FindByName("Follow-Up").ID;<br>int statusID8 = SubjectStatus.FindByName("Long Term Follow-Up").ID;<br>int statusID9 = SubjectStatus.FindByName("Completed").ID;<br><br>DataPoints dp1 = CustomFunction.FetchAllDataPointsForCRDPath("DSDECOD", "DS_1", null, subject);//Screening && Screen Failed<br>// DataPoints dp2 = CustomFunction.FetchAllDataPointsForCRDPath("DSDECOD", "DS_2", null, subject);//Run-In && Run-In Early Terminated<br>// DataPoints dp3 = CustomFunction.FetchAllDataPointsForCRDPath("DSDECOD", "DS_3", null, subject);//Randomized/Registered && Early Terminated<br>DataPoints dp4 = CustomFunction.FetchAllDataPointsForCRDPath("DSDECOD", "DS_4", null, subject);//Randomized/Registered && Early Terminated<br>DataPoints dp5 = CustomFunction.FetchAllDataPointsForCRDPath("DSDECOD", "DS_5", null, subject);//Follow-Up<br>// DataPoints dp6 = CustomFunction.FetchAllDataPointsForCRDPath("DSDECOD", "DS_6", null, subject);//Long Term Follow-Up && Completed<br><br>// Screen Failed<br>subject.SubjectStatus = statusID1;<br>if (dp1.Count > 0 && dp1[0] != null && dp1[0].Active && dp1[0].Data != "" && dp1[0].Data != string.Empty)<br>{<br>　subject.SubjectStatus = statusID2;<br>} | C# |

FIG. 9

1.3    Schedules of Assessments

Table 1    Schedule of Assessments

| Assessments | Screening Period | Treatment Period — 1 (Operation) | | | Follow-up Period |
|---|---|---|---|---|---|
| | | Preoperative | Intraoperative | Postoperative | 7 (Outpatient)[13] |
| Day | -28 to -1 | - | 2 | - | +3 |
| Window | - | - | - | - | - |
| Visit Number | 1 | | 2 | | 3 |
| Informed Consent | X | | | | |
| Inclusion/Exclusion Criteria | X | | | | |
| Medical History | X | | | | |
| Demographics | X | | | | |
| Drug and Alcohol Screen[1] | X[*] | | | | |
| Randomization | | X | | | |
| Physical Examination[2] | X | X | | X[12] | X |
| Vital Signs[3] | X[5] | X | | X[12] | X |
| Clinical Laboratory Tests[4] | X[5] | X | | X[12] | X |
| Height and Body Weight[3] | X | | | | X |
| Serum Pregnancy Test[5] | X[5] | | | | X |
| Routine 12-lead ECG[6] | X | X | | X | X |
| Dosing ASP5354 | | | X | | |
| Blood Sampling for ASP5354 Pharmacokinetics and Metabolite Profiling[7] | | X | X | X | |
| Urine Point Sampling for ASP5354 Pharmacokinetics and Metabolite Profiling[7] | | X | X | | |
| Total Urine Sampling in Catheter Bag and Amount of ASP5354 Excreted in Urine During Surgery[8] | | | X | | |
| Confirmation of urine discoloration[9] | → | | → | → | → |
| Investigator Evaluation for Ureteral Visualization[10] | | | X[10] | | |
| Record Surgery | | | X | | |
| Previous/Concomitant Medications | X | X | X | X | X[14] |
| AE Assessment | X | X | X | X | X[14] |

FIG. 10

```
<Row ss:AutoFitHeight="1">
<Cell ss:StyleID="Protected"><Data ss:Type="String">2</Data></Cell>
<Cell ss:StyleID="Default"><Data ss:Type="String">3</Data></Cell>
<Cell ss:StyleID="Default"><Data ss:Type="String">Day 1 Preoperative</Data></Cell>
<Cell ss:StyleID="Default" ss:Index="6"><Data ss:Type="String">1</Data></Cell>
<Cell ss:StyleID="Default"><Data ss:Type="String">1</Data></Cell>
<Cell ss:StyleID="Default"><Data ss:Type="String">1</Data></Cell>
<Cell ss:StyleID="Default" ss:Index="11"><Data ss:Type="String">FALSE</Data></Cell>
<Cell ss:StyleID="Default"><Data ss:Type="String">77687</Data></Cell>
<Cell ss:StyleID="Default"><Data ss:Type="String">51468</Data></Cell>
</Row>
<Row ss:AutoFitHeight="1">
<Cell ss:StyleID="Protected"><Data ss:Type="String">3</Data></Cell>
<Cell ss:StyleID="Default"><Data ss:Type="String">4</Data></Cell>
<Cell ss:StyleID="Default"><Data ss:Type="String">Day 1 Intraoperative</Data></Cell>
<Cell ss:StyleID="Default" ss:Index="6"><Data ss:Type="String">1</Data></Cell>
<Cell ss:StyleID="Default"><Data ss:Type="String">1</Data></Cell>
<Cell ss:StyleID="Default"><Data ss:Type="String">1</Data></Cell>
<Cell ss:StyleID="Default" ss:Index="11"><Data ss:Type="String">FALSE</Data></Cell>
<Cell ss:StyleID="Default"><Data ss:Type="String">77688</Data></Cell>
<Cell ss:StyleID="Default"><Data ss:Type="String">51469</Data></Cell>
</Row>
<Row ss:AutoFitHeight="1">
<Cell ss:StyleID="Protected"><Data ss:Type="String">4</Data></Cell>
<Cell ss:StyleID="Default"><Data ss:Type="String">5</Data></Cell>
<Cell ss:StyleID="Default"><Data ss:Type="String">Day 1 Postoperative</Data></Cell>
<Cell ss:StyleID="Default" ss:Index="6"><Data ss:Type="String">1</Data></Cell>
<Cell ss:StyleID="Default"><Data ss:Type="String">1</Data></Cell>
<Cell ss:StyleID="Default"><Data ss:Type="String">1</Data></Cell>
<Cell ss:StyleID="Default" ss:Index="11"><Data ss:Type="String">FALSE</Data></Cell>
<Cell ss:StyleID="Default"><Data ss:Type="String">77689</Data></Cell>
<Cell ss:StyleID="Default"><Data ss:Type="String">0</Data></Cell>
</Row>
<Row ss:AutoFitHeight="1">
<Cell ss:StyleID="Protected"><Data ss:Type="String">5</Data></Cell>
<Cell ss:StyleID="Default"><Data ss:Type="String">6</Data></Cell>
<Cell ss:StyleID="Default"><Data ss:Type="String">Day 7 Follow-up</Data></Cell>
<Cell ss:StyleID="Default" ss:Index="6"><Data ss:Type="String">7</Data></Cell>
<Cell ss:StyleID="Default"><Data ss:Type="String">10</Data></Cell>
<Cell ss:StyleID="Default"><Data ss:Type="String">3</Data></Cell>
<Cell ss:StyleID="Default" ss:Index="11"><Data ss:Type="String">FALSE</Data></Cell>
<Cell ss:StyleID="Default"><Data ss:Type="String">77690</Data></Cell>
<Cell ss:StyleID="Default"><Data ss:Type="String">0</Data></Cell>
</Row>
```

FIG.11

```
<Row ss:AutoFitHeight="1">
<Cell ss:StyleID="Default"><Data ss:Type="String">IC_1</Data></Cell>
<Cell ss:StyleID="CenteredCell" ss:Index="3"><Data ss:Type="String">X</Data></Cell>
</Row>
<Row ss:AutoFitHeight="1">
<Cell ss:StyleID="Default"><Data ss:Type="String">IE_1</Data></Cell>
<Cell ss:StyleID="CenteredCell" ss:Index="3"><Data ss:Type="String">X</Data></Cell>
</Row>
<Row ss:AutoFitHeight="1">
<Cell ss:StyleID="Default"><Data ss:Type="String">IE_2</Data></Cell>
<Cell ss:StyleID="CenteredCell" ss:Index="3"><Data ss:Type="String">X</Data></Cell>
</Row>
<Row ss:AutoFitHeight="1">
<Cell ss:StyleID="Default"><Data ss:Type="String">MH_1</Data></Cell>
<Cell ss:StyleID="CenteredCell" ss:Index="12"><Data ss:Type="String">X</Data></Cell>
</Row>
<Row ss:AutoFitHeight="1">
<Cell ss:StyleID="Default"><Data ss:Type="String">DM_1</Data></Cell>
<Cell ss:StyleID="CenteredCell" ss:Index="3"><Data ss:Type="String">X</Data></Cell>
</Row>
<Row ss:AutoFitHeight="1">
<Cell ss:StyleID="Default"><Data ss:Type="String">SU_2</Data></Cell>
<Cell ss:StyleID="CenteredCell" ss:Index="4"><Data ss:Type="String">X</Data></Cell>
</Row>
<Row ss:AutoFitHeight="1">
<Cell ss:StyleID="Default"><Data ss:Type="String">SU_3</Data></Cell>
<Cell ss:StyleID="CenteredCell" ss:Index="4"><Data ss:Type="String">X</Data></Cell>
</Row>
<Row ss:AutoFitHeight="1">
<Cell ss:StyleID="Default"><Data ss:Type="String">PE_1</Data></Cell>
<Cell ss:StyleID="CenteredCell" ss:Index="4"><Data ss:Type="String">X</Data></Cell>
<Cell ss:StyleID="CenteredCell"><Data ss:Type="String">X</Data></Cell>
<Cell ss:StyleID="CenteredCell" ss:Index="7"><Data ss:Type="String">X</Data></Cell>
<Cell ss:StyleID="CenteredCell"><Data ss:Type="String">X</Data></Cell>
</Row>
<Row ss:AutoFitHeight="1">
<Cell ss:StyleID="Default"><Data ss:Type="String">VS_1</Data></Cell>
<Cell ss:StyleID="CenteredCell" ss:Index="4"><Data ss:Type="String">X</Data></Cell>
<Cell ss:StyleID="CenteredCell"><Data ss:Type="String">X</Data></Cell>
<Cell ss:StyleID="CenteredCell" ss:Index="7"><Data ss:Type="String">X</Data></Cell>
<Cell ss:StyleID="CenteredCell"><Data ss:Type="String">X</Data></Cell>
</Row>
```

FIG. 12

| OID | Ordinal | FolderName | Targetdays | EndWinDays | OverDueDays | IsReusable |
|---|---|---|---|---|---|---|
| 2 | 3 | Day 1 Preoperative | 1 | 1 | 1 | FALSE |
| 3 | 4 | Day 1 Intraoperative | 1 | 1 | 1 | FALSE |
| 4 | 5 | Day 1 Postoperative | 1 | 1 | 1 | FALSE |
| 5 | 6 | Day 7 Follow-up | 7 | 10 | 3 | FALSE |

FIG. 13

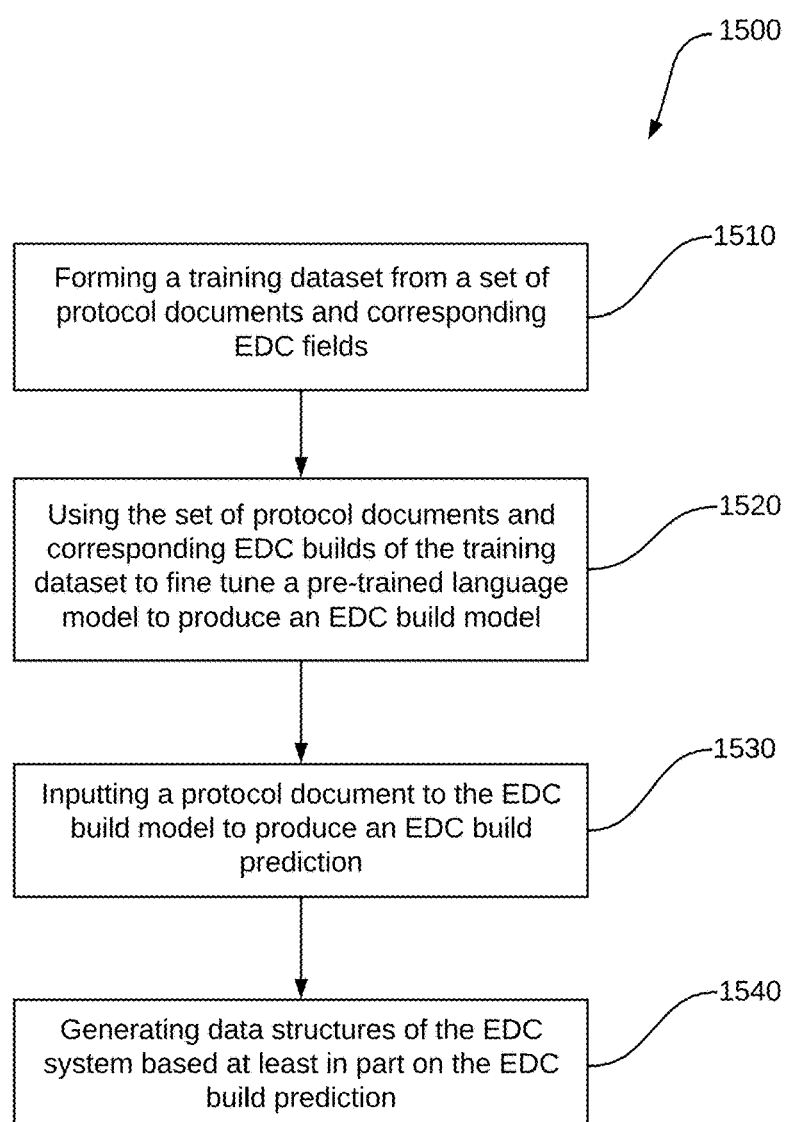

1500

Forming a training dataset from a set of protocol documents and corresponding EDC fields — 1510

Using the set of protocol documents and corresponding EDC builds of the training dataset to fine tune a pre-trained language model to produce an EDC build model — 1520

Inputting a protocol document to the EDC build model to produce an EDC build prediction — 1530

Generating data structures of the EDC system based at least in part on the EDC build prediction — 1540

FIG. 15

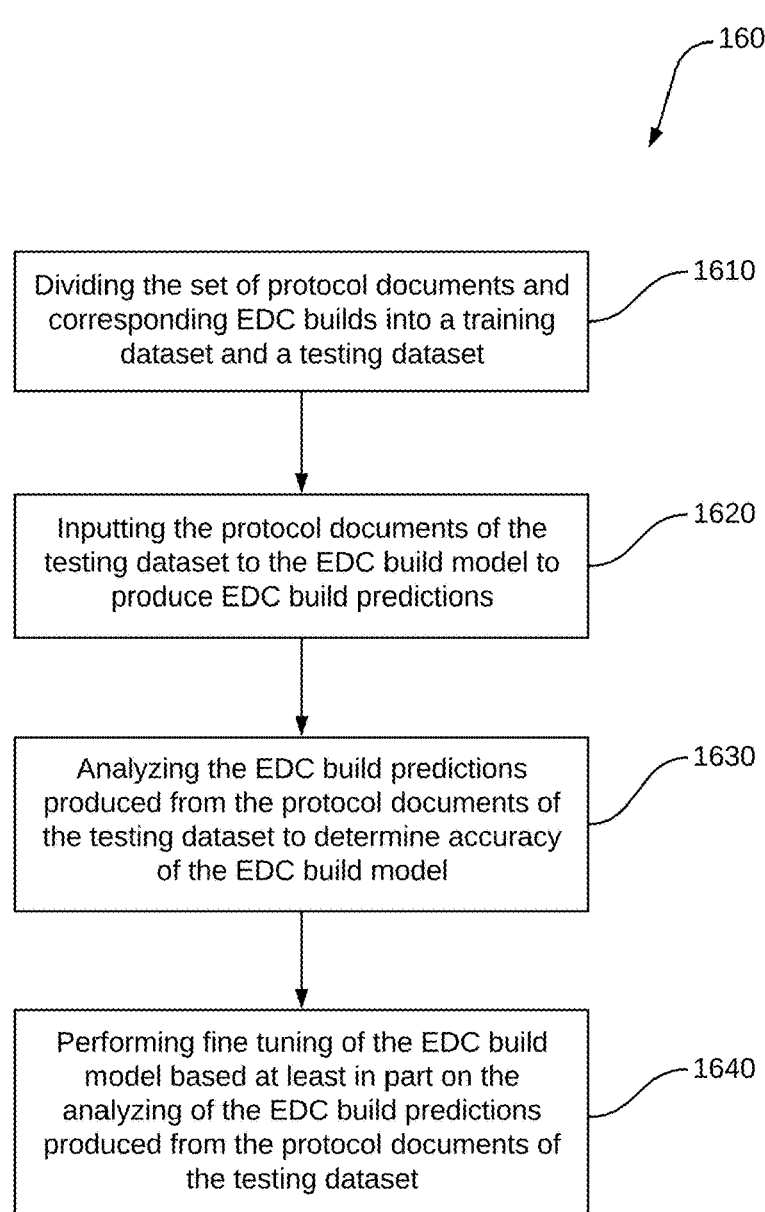

— 1600

Dividing the set of protocol documents and corresponding EDC builds into a training dataset and a testing dataset — 1610

Inputting the protocol documents of the testing dataset to the EDC build model to produce EDC build predictions — 1620

Analyzing the EDC build predictions produced from the protocol documents of the testing dataset to determine accuracy of the EDC build model — 1630

Performing fine tuning of the EDC build model based at least in part on the analyzing of the EDC build predictions produced from the protocol documents of the testing dataset — 1640

SYSTEMS AND METHODS FOR BUILDING AN ELECTRONIC DATA CAPTURE SYSTEM

BACKGROUND

Technical Field

The present disclosure generally relates to building an electronic data capture (EDC) system from a study protocol document.

Description of the Related Art

Electronic Data Capture (EDC) systems provide a framework for designing and managing clinical trials, capturing data from patients and investigators, and ensuring compliance with various requirements. However, designing a new study design or modifying an existing one (e.g., Amendment Changes) for each clinical trial is time-consuming, typically taking about 8-10 weeks. This can delay the commencement of clinical trials, thereby prolonging the overall time-to-market for new therapeutics. The process also requires considerable manual effort and specialized knowledge. This can lead to human errors and inconsistencies, which can negatively impact the quality of the collected data and the integrity of the clinical trial. While some efforts have been made to standardize and automate parts of the EDC setup process, such as the use of Clinical Data Interchange Standards Consortium (CDISC) standards, these solutions still rely heavily on manual effort.

Clinical trials tend to have diverse requirements—every clinical trial is unique and so are its requirements. An EDC system must be adapted to different trial designs, study endpoints, patient populations, etc. Understanding these varied requirements and configuring the EDC system accordingly is labor-intensive. While there are some standard components in an EDC, custom modules or features are typically needed, depending on the study. Furthermore, implementing real-time data validation rules specific to each trial is important for data quality but requires careful design and testing to ensure that discrepancies, outliers, and/or missing data are promptly flagged. Also, given the largely manual nature of conventional EDC study build processes, these approaches lack the scalability needed to efficiently manage multiple simultaneous studies, particularly in larger pharmaceutical companies running several clinical trials concurrently.

SUMMARY

Disclosed herein are approaches that overcome the limitations discussed above by using an EDC build model which is trained to understand a study protocol document in textual form, without standardized formatting or structure, and to generate from this document a machine-readable specification (i.e., an operational database, architecture, or schema) for an EDC system.

In one aspect, the disclosed embodiments provide methods, systems, and computer-readable media for building an electronic data capture (EDC) system. The method includes forming a training dataset from a set of protocol documents and corresponding EDC builds. The method further includes using the set of protocol documents and corresponding EDC builds of the training dataset to fine tune a pre-trained language model to produce an EDC build model. A protocol document is input to the EDC build model to produce an EDC build prediction. Data structures of the EDC system are generated based at least in part on the EDC build prediction.

Embodiments may include one or more of the following features, alone or in combination.

The generating of the data structures of the EDC system may include generating one or more electronic case report forms, generating one or more edit checks for checking data as it is input via the one or more electronic case report forms, and generating one or more folder structures for managing EDC system information. The using of the set of protocol documents and corresponding EDC builds of the training dataset to fine tune the pre-trained language model may include adjusting hyperparameters of the pre-trained language model. The protocol document may be a natural language text document. The protocol document may include a schedule of assessments in tabular form. The EDC build prediction may be in the form of an extensible markup language (XML) document. The forming of the training dataset may include dividing the set of protocol documents and corresponding EDC builds into the training dataset and a testing dataset. The forming of the training dataset may further include inputting the protocol documents of the testing dataset to the EDC build model to produce EDC build predictions; and analyzing the EDC build predictions produced from the protocol documents of the testing dataset to determine accuracy of the EDC build model. The method may include performing fine tuning of the EDC build model based at least in part on the analyzing of the EDC build predictions produced from the protocol documents of the testing dataset.

BRIEF DESCRIPTION OF THE DRAWINGS

FIG. 2 is an example excerpt of a study protocol document which discusses the inclusion criteria of a study in natural language text.

FIGS. 3 and 4 each depict a portion of a simulated EDC build, in the form of an XML specification, generated by the EDC build model based on the excerpt of the study protocol document shown in FIG. 2.

FIG. 6 depicts the XML-specified EDC build of FIG. 4 converted into the form of a "data dictionary entries" spreadsheet which is part of the alternative spreadsheet-specified version of the EDC build.

FIG. 7 is an example excerpt of a study protocol document which discusses in natural language the criteria for screen failures of a study.

FIG. 8 depicts a portion of a simulated EDC build, in the form of an XML specification, generated by the EDC build model based on the excerpt of the study protocol document shown in FIG. 7.

FIG. 9 depicts the XML-specified EDC build of FIG. 8 converted into the form of a "custom functions" spreadsheet which is part of an alternative spreadsheet-specified version of the EDC build.

FIG. 10 is an example excerpt of a study protocol document which discusses a schedule of assessments of a study in natural language, which is in the form of a table.

FIGS. 11 and 12 each depict a portion of a simulated EDC build, in the form of an XML specification, generated by the EDC build model based on the excerpt of the study protocol document shown in FIG. 10.

FIG. 13 depicts the XML-specified EDC build of FIG. 11 converted into the form of a "folders" spreadsheet which is part of an alternative spreadsheet-specified version of the EDC build.

FIG. 15 depicts a method of building an electronic data capture (EDC) system.

FIG. 16 depicts further aspects of the method of building an electronic data capture (EDC) system.

FIG. 17 depicts a user interface screen showing the generation of an edit check relating to the dates of an adverse event using a demonstration EDC build model.

Figure 1:
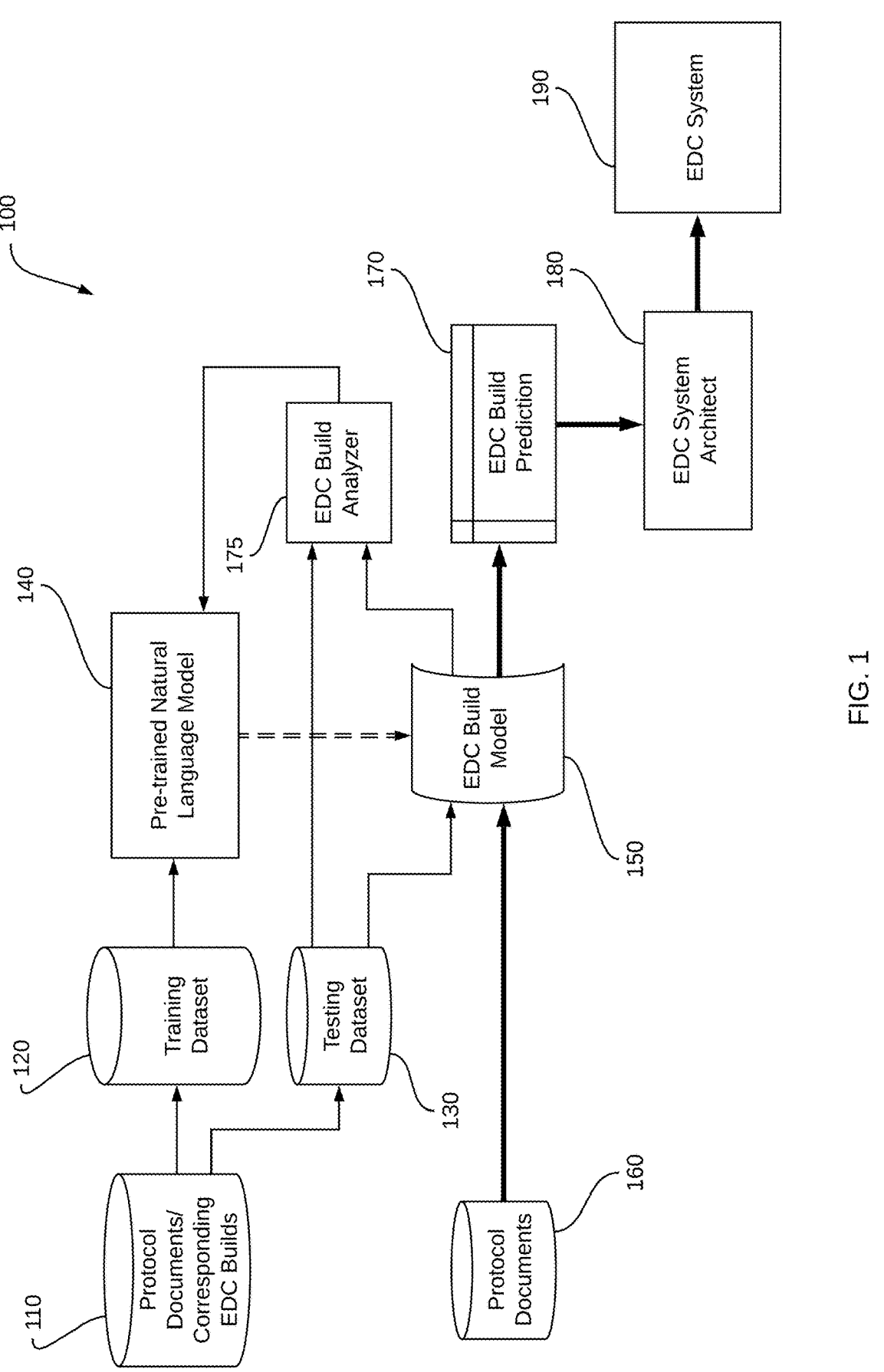
FIG. 1 depicts a system for building an electronic data capture (EDC) system, according to disclosed embodiments.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

The disclosed embodiments address the technical problems associated with building electronic data capture (EDC) systems to significantly reduce the time and manual effort involved in setting up a new clinical trial in an EDC system. In some cases, a typical timeline of 8-10 weeks for creating an EDC study build may be reduced to a fraction of that period, e.g., 1-2 weeks or less. This allows clinical trials to start sooner, thereby reducing overall time-to-market for new therapeutics. The EDC build model described herein reduces the potential for human error in the EDC study build process, which increases the accuracy and consistency of the generated databases. Furthermore, the disclosed approaches facilitate the concurrent setup of multiple EDC study builds, providing much-needed scalability for larger pharmaceutical companies running concurrent clinical trials.

The disclosed embodiments provide an artificial intelligence (AI) model that learns and improves over time, which enhances its ability to handle increasingly complex clinical trial protocols. This adaptability is a significant advantage as clinical trials continue to evolve and grow in complexity. Furthermore, by using AI models, the disclosed approaches also offer the potential for more standardized study builds, which can enhance data interoperability and streamline regulatory compliance processes. Thus, compared to conventional techniques for creating EDC study builds, the disclosed embodiments provide significant advancements in speed, accuracy, efficiency, and scalability, resulting in a valuable innovation in the field of clinical trials.

FIG. 1 is a block diagram of a system 100 for building an electronic data capture (EDC) system. The system uses artificial intelligence (AI) in conjunction with a dataset 110 of protocol documents and corresponding EDC builds. The EDC builds correspond to the protocol documents in that they are derived from the protocol documents—either through manual effort or by using a trained model in accordance with disclosed embodiments. A study protocol is a text document, e.g., natural language text, containing information on overall study design, objectives, patient cohorts, and procedures, etc. (examples of excerpts of study protocols can be seen, e.g., in FIGS. 2, 7, and 10). An EDC build, on the other hand, is a machine-readable specification and/or schema, such as an Extensible Markup Language (XML) specification (examples of XML-specified portions of EDC builds can be seen, e.g., in FIGS. 3, 4, 8, 11, and 12). The EDC build serves, in effect, as an operational database which defines the various data structures used in a study, such as electronic case report forms (eCRF), data fields of the eCRF, edit checks to validate input data, folder structures for storing the input data, etc. In conventional approaches, an EDC build is manually created based on a study protocol.

The dataset 110 (and, similarly, the set of protocol documents 160) is produced by receiving a study protocol as an input. The study protocol is typically a text document (e.g., a PDF or Word document) that outlines all aspects of the clinical trial, such as objectives, design, methodology, statistical considerations, and organization. The input document is preprocessed to extract and structure the relevant information. Preprocessing may involve steps such as tokenization (i.e., breaking text into individual words or terms), lemmatization (i.e., reducing words to their base or root form), and removing stop words (i.e., filtering out common words that do not contribute to meaning).

The dataset 110 is split into a training dataset 120 and a testing dataset 130. For example, 80% of the dataset 110 may be used for training while 20% is held back to use for testing. The set of protocol documents and corresponding EDC builds of the training dataset 120 are used to fine tune a pre-trained language model 140 to produce an EDC build model 150. In embodiments, the pre-trained language model 140 may be a widely available Natural Language Processing (NLP) model, such as Pathways Language Model (PaLM) from Google Research or Large Language Model Meta AI (LLaMA) from Meta.

Fine tuning a pre-trained model involves performing further training of the model with specific training data, e.g., the dataset 110 of protocol documents and corresponding EDC builds, and adjusting the parameters of the model so that it performs better on the specific dataset. During this process, the model learns to associate an input (e.g., clinical trial protocol documents) with an output (e.g., corresponding EDC study builds). It does this by adjusting its internal parameters to minimize the difference between its predictions and the actual outputs in the training data. In embodiments, the fine tuning of the pre-trained language model 140 may include, for example, adjusting hyperparameters of the pre-trained language model 140. This approach leverages the broad knowledge captured during pre-training on massive datasets while adapting the model to a specialized task or domain with a smaller dataset.

The dashed line between the language model 140 and the EDC build model 150 in FIG. 1 signifies that once the language model 140 has been fine-tuned, it is used as a runtime model, i.e., the EDC build model 150 in this example. The EDC build model 150 is trained on numerous clinical trial protocols and corresponding EDC study builds.

This training allows the EDC build model 150 to make accurate predictions on new, unseen study protocols.

In runtime operation, a protocol document may be taken from a dataset 160 of protocol documents and input to the EDC build model 150 to produce an EDC build prediction 170. The dataset 160 of protocol documents may include, for example, unseen protocols for studies which are in the EDC system design phase. In embodiments, the EDC build predictions 170 may be manually analyzed to assess how well they conform to expectations. Adjustments may then be made to improve the accuracy of the EDC build model 150 based on this analysis.

In embodiments, users interact with the system 100 via a user interface where they can upload the study protocol, initiate the processing, and download the generated EDC study build. Users can also provide feedback on the generated output, which can be used to further improve the system's performance. The user interface may include a communication element, e.g., a chatbot, to explain the various aspects of the study build (e.g., how to set up edit checks).

The EDC build prediction 170 is input to an EDC system architect 180, such as, for example, Medidata® Architect™. The EDC system architect 180 uses the information in the EDC build prediction 170 to generate data structures of the EDC system 190, such as electronic case report forms (eCRF), data fields of the various forms, edit checks to validate input data, and folder structures for storing the input data. In embodiments, the EDC build prediction 170 may be an Architecture Loader Specification (ALS) file in extensible markup language (XML) form, which specifies the forms, fields, etc., in a specific format which can be used by Medidata® Architect™ to generate the data structures of a Medidata Rave® EDC system. In embodiments, the EDC system architect 180 may be incorporated as part of the EDC system 190, In implementations, one may design a study using tools provided by the software of an EDC system, such as Medidata Rave®, which provides user interface screens for defining fields, rules, etc. (see, e.g., FIG. 18). The completed study design, i.e., study build, can be downloaded for review and approval. The downloadable study build file is referred to as an Architect Loader Specification (ALS) file, which may be in the form of an XML specification (which may be embodied by an XML file). The XML file can be opened using either a text editor or, alternatively, a spreadsheet application (e.g., Microsoft Excel). If an ALS file is opened using a text editor, then it appears in a form similar to that depicted in FIGS. 3, 4, 8, 11, and 12. If the ALS file is opened as a spreadsheet, i.e., converted into the form of a spreadsheet, then it appears in a form similar to that depicted in FIGS. 5, 6, 9, 13, and 14 (in implementations, the spreadsheets depicted in these figures may be separate tabs in a spreadsheet "workbook" and may, in combination, constitute the ALS of a particular study build). As noted above, in spreadsheet form, an XML file for a study build can be more easily examined and modified. In either case, the downloaded study build file can be used to create and/or update a study. This allows a user to reuse, and modify, existing study designs without manual entry of design parameters.

As explained above, the dataset 110 is split into a training dataset 120 and a testing dataset 130. In embodiments, the protocol documents of the testing dataset 120 may be input to the trained EDC build model 150 to produce EDC build predictions 170. An EDC build analyzer 175 receives the EDC build predictions 170 based on the testing dataset 130 and also receives the corresponding protocol document directly from the testing dataset 130. This allows the EDC build analyzer 175 to analyze the EDC build predictions 170 produced from the protocol documents of the testing dataset 130 to assess the accuracy of the EDC build model 150. The results of the analysis by the EDC build analyzer 175, based on the testing dataset 130, may be used to perform further fine tuning of the EDC build model 150.

As explained above, a set of study protocol documents and a set of corresponding EDC builds are used as a dataset 110 to fine tune a pre-trained language model 140. An EDC build defines the various data structures used by the EDC system 190, such as electronic case report forms (eCRF), data fields of the eCRF, edit checks to validate input data, folder structures for storing the input data, etc. EDC builds may be retrieved from a study management software system, such as, for example, Medidata Rave®. In embodiments, the EDC builds may be Architecture Loader Specification (ALS) files in XML form.

A study protocol is a text document, e.g., natural language text, containing information on overall study design, objectives, patient cohorts, and procedures, etc. For example, a study protocol may include: the background and rationale, the objectives (e.g., primary, secondary, and exploratory objectives), type (e.g., randomized, double-blind, placebo-controlled), the number of subjects, the duration and phases, inclusion and exclusion criteria, assessments and procedures (e.g., details of medical examinations and laboratory tests, schedules of events or visits, etc.), treatment of subjects (e.g., the investigational product, dosage, and method of administration), procedures for monitoring drug efficacy and safety, definitions and procedures for adverse events and serious adverse events, data management and statistical methods, quality control and quality assurance, ethical considerations, publication and data sharing policies, references to relevant scientific literature, and various types of forms (e.g., informed consent, questionnaires, surveys, etc.).

Although study protocol documents for different studies generally include similar information, such documents do not have a universally standardized structure and/or content. Moreover, such documents may vary widely in terms of text formatting, font, punctuation, etc. (see, e.g., excerpts of study protocol documents in FIGS. 2, 7, and 10). Study protocol documents are intended to be read by people performing various roles in the study, e.g., study designers, regulators, clinicians, etc., as opposed to being used solely for designing a study.

In implementations, study protocols used as part of the training dataset may be obtained from a common repository (e.g., ClinicalTrials.gov) or from an internal document management system, in cases in which a study developer has a repository of such information. Various preprocessing tasks may be performed on the study protocols, such as removing irrelevant information and/or standardizing the format of the input data.

FIG. 2 is an example excerpt of a study protocol document which discusses, in natural language, the inclusion criteria of a study. It is an example of the type of document that can be used in a dataset 160 of protocol documents to be input to the EDC build model 150 to produce an EDC build prediction 170 (see FIG. 1). In conventional approaches, such criteria would be incorporated into the EDC system manually, for example, by studying and interpreting the protocol document and creating input fields and rules in an electronic case report form (eCRF) relating to eligibility review.

FIGS. 3 and 4 each depict a portion of a simulated EDC build, in the form of an XML specification, generated by the EDC build model 150 based on the excerpt of the study protocol document shown in FIG. 2. The EDC build is derived from the study protocol document, e.g., by using a trained EDC build model 150 (see FIG. 1) in accordance with disclosed embodiments. Such an EDC build may be used in the dataset 110 of protocol documents and corresponding EDC builds (paired with its corresponding protocol document) and/or to generate the data structures of an EDC system 190. The XML statements in this example define fields of an eCRF for the input of data relating to subject eligibility. In embodiments, the EDC build may be an Architecture Loader Specification (ALS) file in XML form, which specifies the forms, fields, etc., in a specific format which can be used by Medidata® Architect™ to generate the data structures of a Medidata Rave® EDC system.

Figure 5:
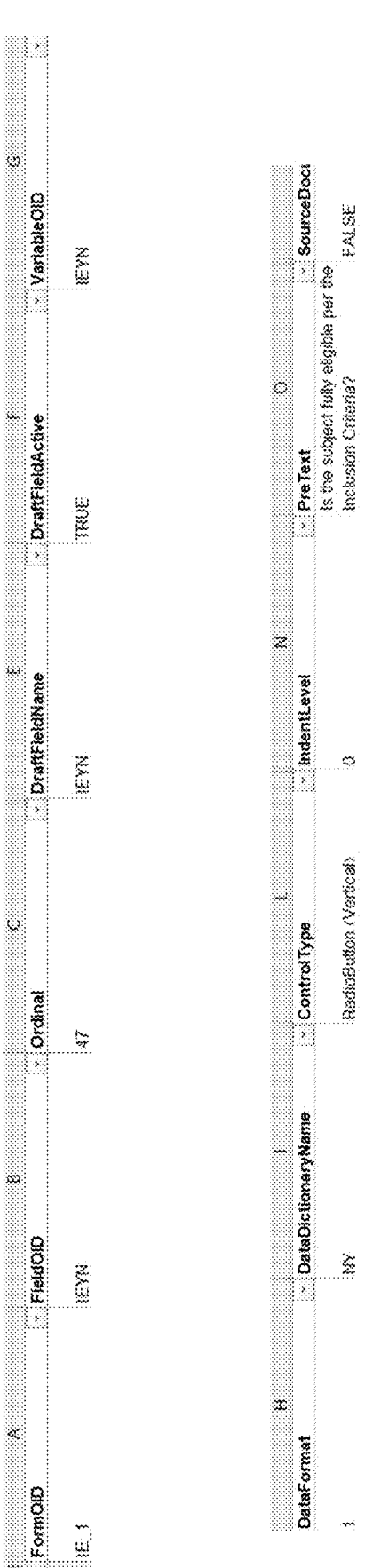
FIG. 5 depicts the XML-specified EDC build of FIG. 3 converted into the form of a "fields" spreadsheet which is part of an alternative spreadsheet-specified version of the EDC build, with each row of the sheet defining a particular field of the eCRF forms.

FIG. 5 depicts the XML-specified EDC build of FIG. 3 converted into the form of a "fields" spreadsheet which is part of an alternative spreadsheet-specified version of the EDC build. Each row of the sheet defines a particular field of the eCRF forms. The spreadsheet format allows a study designer to more easily examine and modify the various components of a study build. In implementations, one may design a study using Medidata Rave®, which provides user interface screens for defining fields, rules, etc. (see, e.g., FIG. 18). The completed study design, i.e., study build, can be downloaded for review and approval.

The downloadable study build file is referred to as an Architect Loader Specification (ALS) file, which may be in the form of an XML specification. The XML file can be opened using either a text editor or, alternatively, a spreadsheet application (e.g., Microsoft Excel). If an ALS file is opened using a text editor, then it appears in a form similar to that depicted in FIGS. 3, 4, 8, 11, and 12. If the ALS file is opened as a spreadsheet, i.e., converted into a spreadsheet, then it appears in a form similar to that depicted in FIGS. 5, 6, 9, 13, and 14. As noted above, in the alternative spreadsheet form, an XML file for a study build can be more easily examined in modified. In either case, the downloaded study build file can be used to create and/or update a study. This allows a user to reuse, and modify, existing study designs without manual entry of design parameters.

In this example, a field for the variable "IEYN" is defined on form "IE_1," which is an inclusion/exclusion criteria form. In embodiments, the variable IEYN has a yes or no ("Y" or "N") value which indicates whether or not a subject has met all of the inclusion criteria (in which case the value would be "Y"). The control type on the form is specified as a vertical radio button, which would allow a user to click on the button and select "Y" or "N" for the value of this variable. A "PreText" string is specified to provide a prompt (e.g., "is the subject fully eligible per the inclusion criteria?") to the user inputting the data.

FIG. 6 depicts the XML-specified EDC build of FIG. 4 converted into the form of a "data dictionary entries" spreadsheet which is part of the alternative spreadsheet-specified version of the EDC build. The spreadsheet format allows a study designer to more easily examine and modify the various components of a study build. Each row of the sheet defines an entry in a dictionary of user data strings. The ability to define data dictionary entries allows the designer to standardize components of the study build, e.g., fields, rules, etc., and to save time in the study design process. In this example, the study designer has created a data dictionary with all of the inclusion criteria. A doctor entering data via the inclusion/exclusion forms of the EDC is asked "if the subject is not eligible for this study, which of these inclusion criteria did they not meet.?" These same prompts may be used in other contexts by referencing the dictionary entries.

In the example depicted, the dictionary named "IETESTI" has a number of entries, each associated with a "CodedData" parameter, e.g., IN02, IN03, IN04, etc. For example, if this parameter is assigned the code "IN02," then the corresponding data string would be: "2. Subject is scheduled to undergo laparoscopic/minimally invasive colorectal surgery." This string may be used as a user prompt on one or more forms of the defined eCRF. Among other advantages, the use of a dictionary for such strings allows for the strings to be reused efficiently and consistently throughout the defined EDC system.

FIG. 7 is an example excerpt of a study protocol document which discusses in natural language the criteria for screen failures (i.e., screening failures) of a study and the requirements as to how these must be handled. Such criteria would be incorporated into the EDC system, for example, by including input fields and rules in electronic case report forms (eCRF) relating to eligibility review.

Figure 8:
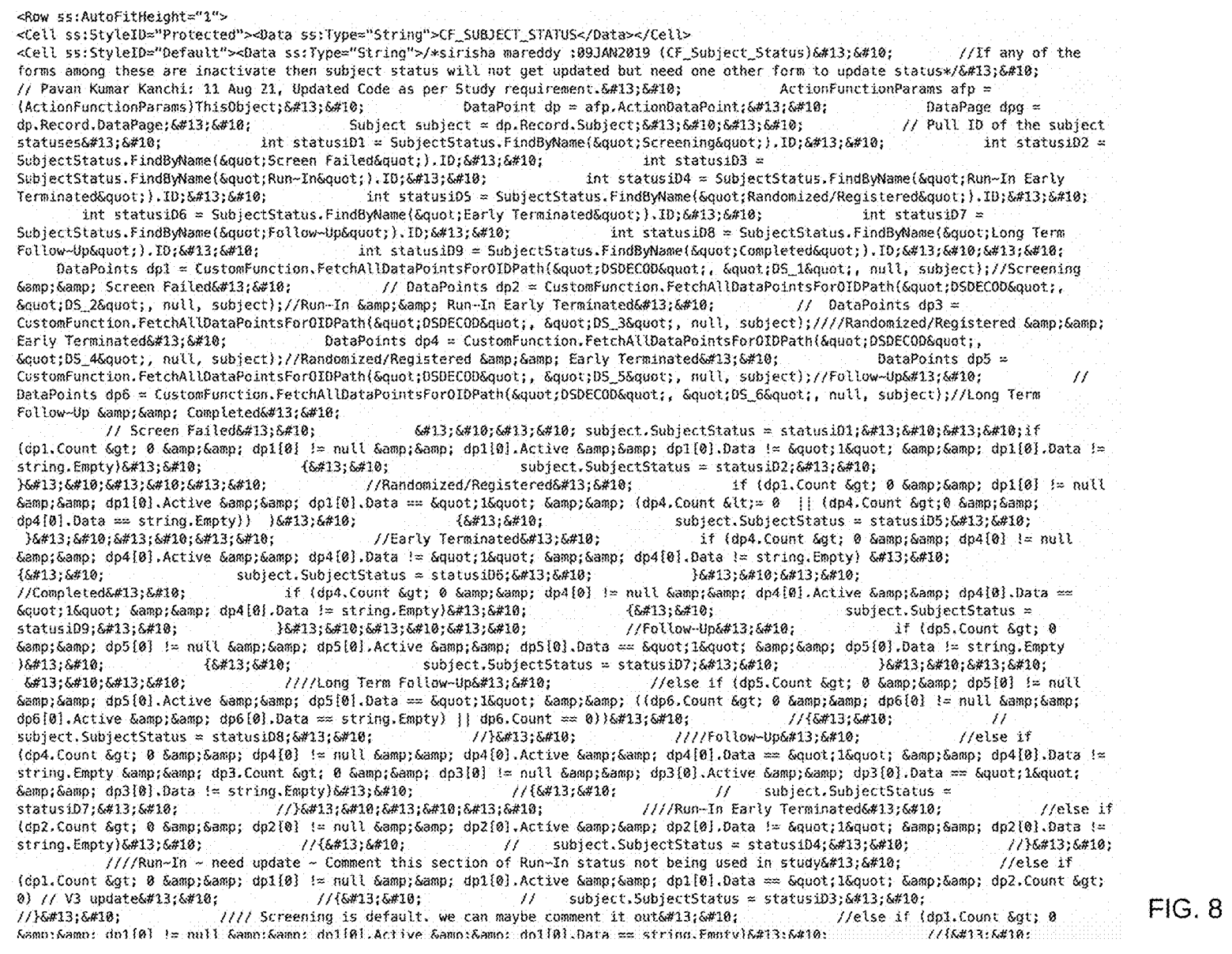

FIG. 8 depicts a portion of a simulated EDC build, in the form of an XML specification, generated by the EDC build model based on the excerpt of the study protocol document shown in FIG. 7. The EDC build is derived from the study protocol document, e.g., by using a trained model in accordance with disclosed embodiments. The XML statements in this portion of the EDC build define a "custom function" (CF_SUBJECT_STATUS) relating to subject status. When building edit checks, i.e., data validation, the EDC system may offer a set number of parameters for performing common types of checks. For example, copying data from one field to another or opening a question to the doctor (e.g., "are you sure this is the right temperature?").

Custom functions allow a study designer to set up more specialized and/or complex data validations. For example, a study designer may wish to set the status of a subject based on a specific set of conditions. To trigger a custom function, the designer sets up an edit check with defined parameters: Checks, CheckSteps, and CheckAction. The CheckAction is the desired action, which in this example is to trigger the custom function code (e.g., CF_SUBJECT_STATUS). The Checks and CheckSteps define the values and functions, respectively, for the edit check to perform. In this particular case, there are more than one edit checks that trigger this custom function (e.g., DS1_SUBJECT_STATUS).

FIG. 9 depicts the XML-specified EDC build of FIG. 8 converted into the form of a "custom functions" spreadsheet which is part of an alternative spreadsheet-specified version of the EDC build. The spreadsheet format allows a study designer to more easily examine and modify the various components of the study build. Each row of the sheet defines a custom function, including the function name, source code, and programming language (e.g., C#). As explained above, custom functions are a component of a study build, along with folders, forms, fields, edit checks, etc. Custom functions provide more complex types of edit checks to be more easily integrated into the study build.

FIG. 10 is an example excerpt of a study protocol document which discusses a schedule of assessments of a study in natural language, which is in the form of a table. The information includes the assessments to be performed, such as informed consent, physical examination, laboratory tests, etc., versus the particular period in which the assessments are to be performed, such as the screening period, treatment period, and follow-up period.

FIGS. 11 and 12 each depict a portion of a simulated EDC build, in the form of an XML specification, generated by the EDC build model based on the excerpt of the study protocol document shown in FIG. 10. The EDC build corresponds to the excerpt of the study protocol document in that is derived from the study protocol document, e.g., by using a trained model in accordance with disclosed embodiments. The XML statements define an eCRF for the input of data relating to subject status FIG. 13 depicts the XML-specified EDC build of FIG. 11 converted into the form of a "folders" spreadsheet which is part of an alternative spreadsheet-specified version of the EDC build. The spreadsheet format allows a study designer to more easily examine and modify the various components the study build. Each row of the sheet defines a folder associated with a particular period or phase of the study, e.g., screening, treatment, of follow up, shown as column headings of the table presented in the excerpt of the study protocol document shown in FIG. 10.

Figure 14:
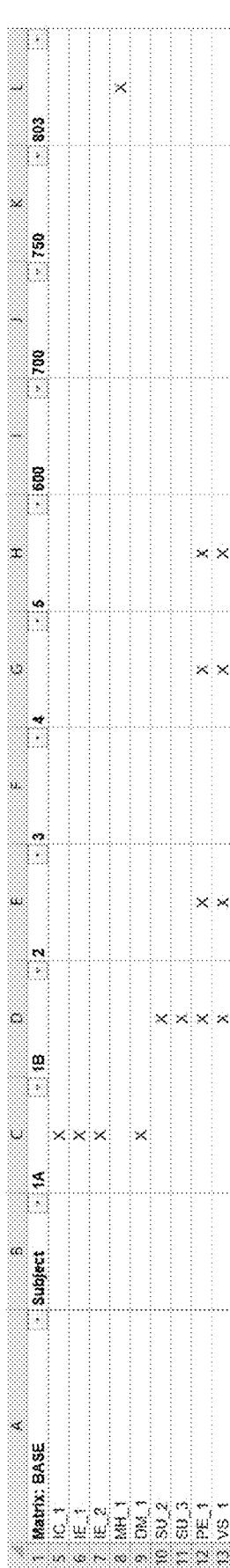
FIG. 14 depicts the XML-specified EDC build of FIG. 12 converted into the form of a "BASE matrix" spreadsheet which is part of an alternative spreadsheet-specified version of the EDC build.

FIG. 14 depicts the XML-specified EDC build of FIG. 12 converted into the form of a "BASE matrix" spreadsheet which is part of an alternative spreadsheet-specified version of the EDC build. Each row of the sheet corresponds to an assessment to be performed, e.g., Informed Consent (IC_1), Inclusion/Exclusion Criteria (IE_1, IE_2), Medical History (MH_1), etc., shown as row headings of the table presented in the excerpt of the study protocol document shown in FIG. 10.

FIG. 15 depicts a method 1500 of building an electronic data capture (EDC) system. The method 1500 includes forming a training dataset from a set of protocol documents and corresponding EDC builds (1510). The method 1500 further includes using the set of protocol documents and corresponding EDC builds of the training dataset to fine tune a pre-trained language model to produce an EDC build model (1520). The method 1500 further includes inputting a protocol document to the EDC build model to produce an EDC build prediction (1530). The method 1500 further includes generating data structures of the EDC system based at least in part on the EDC build prediction (1540).

FIG. 16 depicts a method 1600 including further aspects of the method 1500 of building an electronic data capture (EDC) system, the further aspects relating to testing of the EDC build model. The method 1600 includes dividing the set of protocol documents and corresponding EDC builds into a training dataset and a testing dataset (1610). The method 1600 further includes inputting the protocol documents of the testing dataset to the EDC build model to produce EDC build predictions (1620). The method 1600 further includes analyzing the EDC build predictions produced from the protocol documents of the testing dataset to determine accuracy of the EDC build model (1630). The method 1600 further includes performing fine tuning of the EDC build model based at least in part on the analyzing of the EDC build predictions produced from the protocol documents of the testing dataset (1640).

Figure 17:
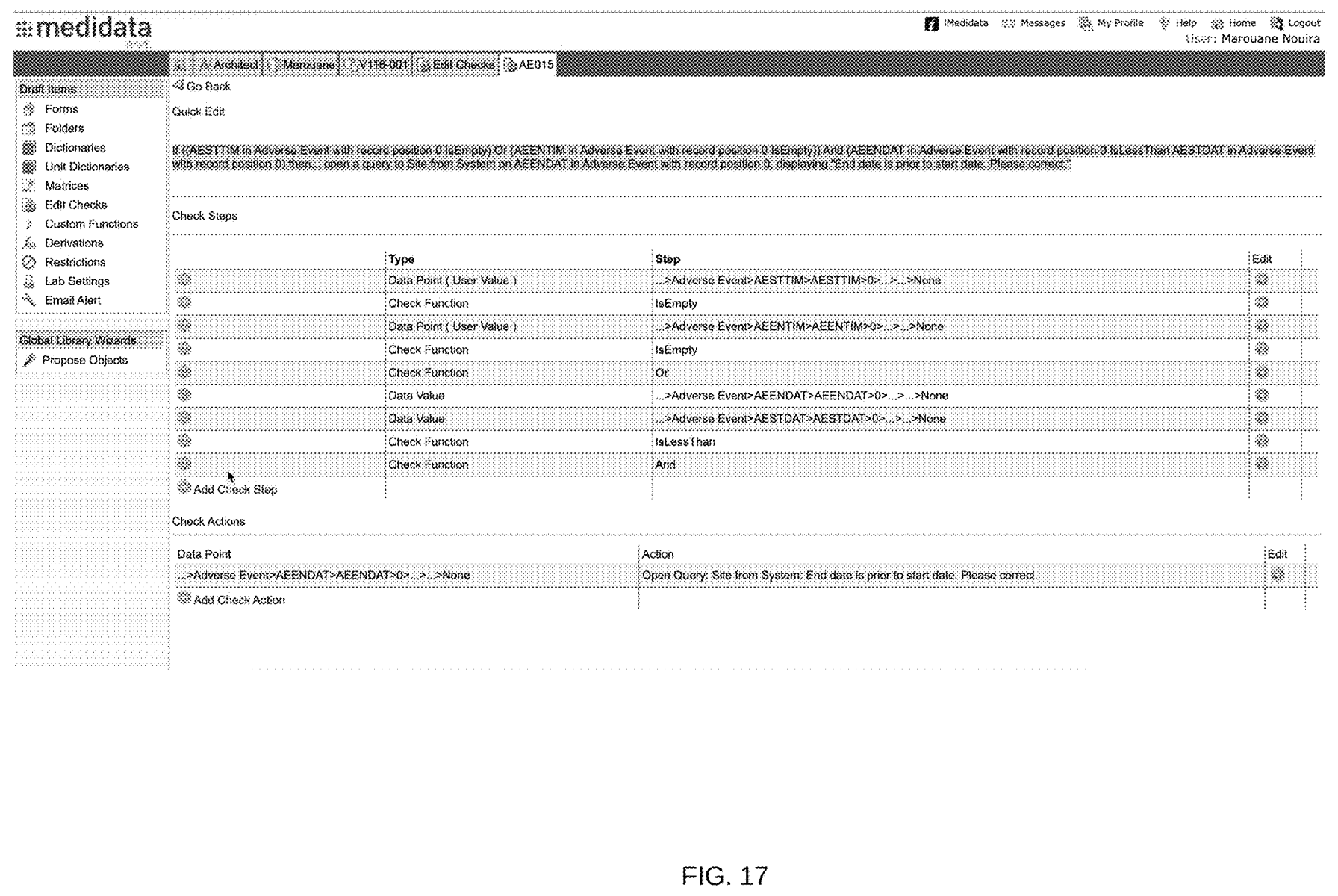

FIG. 17 is a user interface screen showing the generation of an edit check relating to the dates of an adverse event using a demonstration EDC build model. The edit check includes a series of check steps and a check action in which a user is prompted to correct an error in the start and end dates, e.g., due to the end date being prior to the start date. In disclosed embodiments, the elements of an edit check are generated by processing corresponding portions of a study protocol document. In the depicted demonstration, a text string specifying the edit check was entered to generate the edit check depicted in the figure. In the demonstration, the entry and conversion of the text string into the edit check took about 15 minutes.

Figure 18:
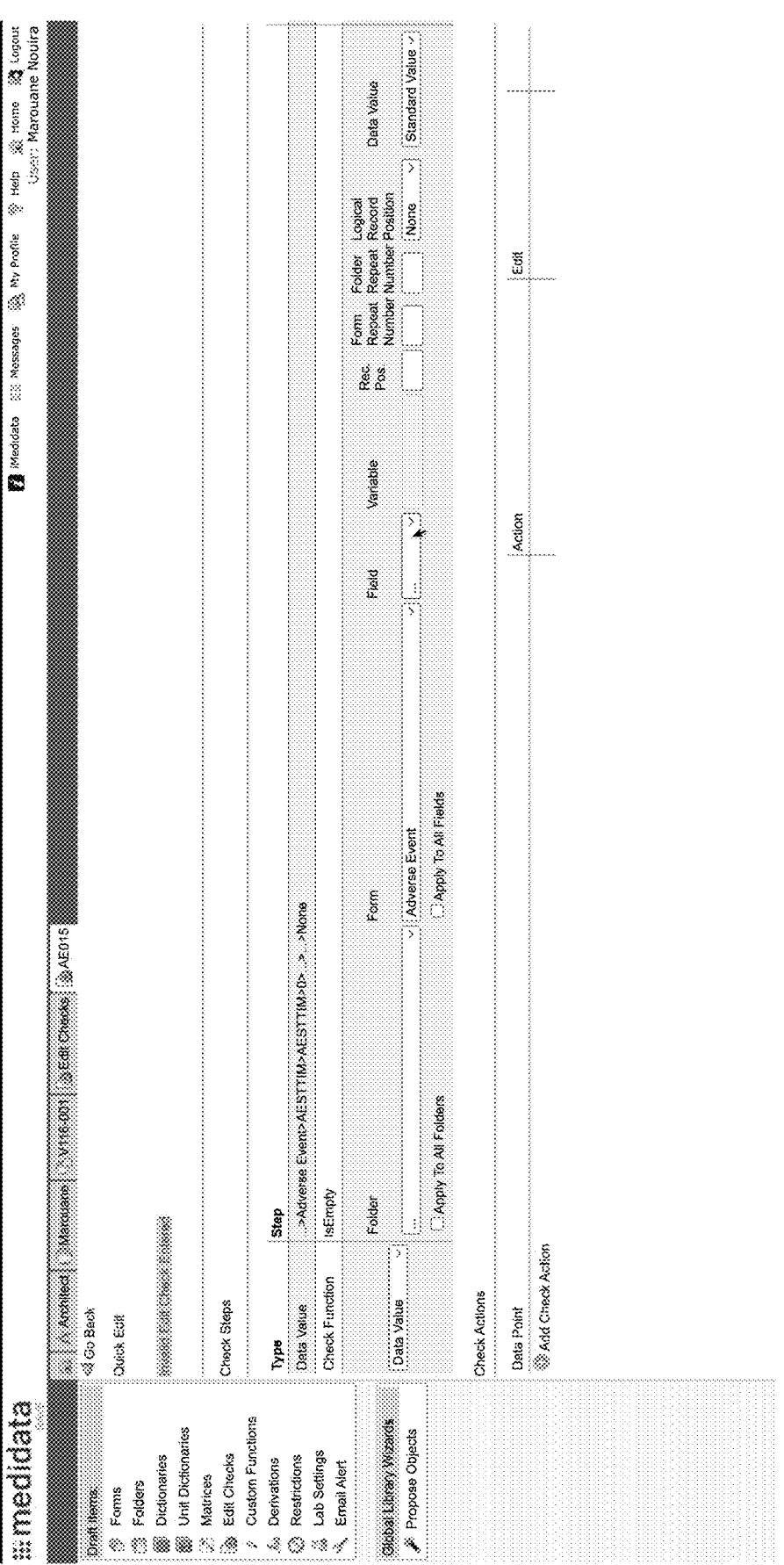
FIG. 18 depicts a user interface screen for manually inputting elements of an edit check relating to the dates of an adverse event of a demonstration EDC build.

FIG. 18 a user interface screen for manually inputting elements of an edit check relating to the dates of an adverse event of a demonstration EDC build. The example depicted shows a data value element of the edit check being entered by inputting data values and/or selecting various parameters, such as event type. In the demonstration, the manual entry of the various data values and parameters of the edit check took over two hours to complete.

While the implementations presented herein focus on clinical trials (e.g., for pharmaceutical research), the disclosed approaches may be used in other areas in which structured data collection and management are complex. These solutions could be used in other applications (and other fields) for which build and/or development is time consuming and laborious.

Aspects of the present invention may be embodied in the form of a system, a computer program product, or a method. Similarly, aspects of the present invention may be embodied as hardware, software, or a combination of both. Aspects of the present invention may be embodied as a computer program product saved on one or more computer-readable media in the form of computer-readable program code embodied thereon.

The computer-readable medium may be a computer-readable storage medium. A computer-readable storage medium may be, for example, an electronic, optical, magnetic, electromagnetic, infrared, or semiconductor system, apparatus, or device, or any combination thereof.

Computer program code in embodiments of the present invention may be written in any suitable programming and/or scripting language. The program code may execute on a single computer, or on a plurality of computers. The computer may include a processing unit in communication with a computer-usable medium, where the computer-usable medium contains a set of instructions, and where the processing unit is designed to carry out the set of instructions, and/or a trained machine learning algorithm.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method of building an electronic data capture (EDC) system, the method comprising:

forming a training dataset from a set of clinical trial protocol documents and corresponding EDC builds, each EDC build comprising a machine-readable specification file defining electronic case report form (eCRF) data fields, edit checks for validating data entered into the eCRF data fields, and folder structures for storing study data within the EDC system;

using the set of clinical trial protocol documents and corresponding EDC builds of the training dataset to tune a pre-trained language model to produce an EDC build model;

inputting a clinical trial protocol document to the EDC build model to produce an EDC build prediction comprising a corresponding machine-readable specification file; and generating data structures of the EDC system based at least in part on the EDC build prediction by loading the machine-readable specification file into an EDC system platform to instantiate the eCRF data fields, the edit checks for validating the data entered into the eCRF data fields, and the folder structures for storing study data within the EDC system.

2. The method of claim 1, wherein said generating data structures of the EDC system comprises generating one or more electronic case report forms.

3. The method of claim 1, wherein said generating data structures of the EDC system comprises generating one or more folder structures for managing EDC system information.

4. The method of claim 1, wherein said using the set of protocol documents and corresponding EDC builds of the training dataset to tune the pre-trained language model comprises adjusting hyperparameters of the pre-trained language model.

5. The method of claim 1, wherein the protocol document is a natural language text document.

6. The method of claim 5, wherein the protocol document comprises a schedule of assessments in tabular form.

7. The method of claim 1, wherein the EDC build prediction is in the form of an extensible markup language (XML) document.

8. The method of claim 1, wherein said forming the training dataset comprises dividing the set of protocol documents and corresponding EDC builds into the training dataset and a testing dataset.

9. The method of claim 8, further comprising:
inputting the protocol documents of the testing dataset to the EDC build model to produce EDC build predictions; and
analyzing the EDC build predictions produced from the protocol documents of the testing dataset to determine accuracy of the EDC build model.

10. The method of claim 9, further comprising performing tuning of the EDC build model based at least in part on said analyzing the EDC build predictions produced from the protocol documents of the testing dataset.

11. A system for building an electronic data capture (EDC) system, the system comprising:
a computer having one or more processors in communication with a memory, the memory storing instructions executable by said one or more processors to perform:
forming a training dataset from a set of clinical trial protocol documents and corresponding EDC builds, each EDC build comprising a machine-readable specification file defining electronic case report form (eCRF) data fields, edit checks for validating data entered into the eCRF data fields, and folder structures for storing study data within the EDC system;
using the set of clinical trial protocol documents and corresponding EDC builds of the training dataset to tune a pre-trained language model to produce an EDC build model;
inputting a clinical trial protocol document to the EDC build model to produce an EDC build prediction comprising a corresponding machine-readable specification file; and
generating data structures of the EDC system based at least in part on the EDC build prediction by loading the machine-readable specification file into an EDC system platform to instantiate the eCRF data fields, the edit checks for validating the data entered into the eCRF data fields, and the folder structures for storing study data within the EDC system.

12. The system of claim 11, wherein said generating data structures of the EDC system comprises generating one or more electronic case report forms.

13. The system of claim 11, wherein said generating data structures of the EDC system comprises generating one or more folder structures for managing EDC system information.

14. The system of claim 11, wherein the EDC build prediction is in the form of an extensible markup language (XML) document.

15. The system of claim 11, wherein said forming the training dataset comprises dividing the set of protocol documents and corresponding EDC builds into the training dataset and a testing dataset.

16. The system of claim 15, further comprising:
inputting the protocol documents of the testing dataset to the EDC build model to produce EDC build predictions; and
analyzing the EDC build predictions produced from the protocol documents of the testing dataset to determine accuracy of the EDC build model.

17. The system of claim 16, further comprising performing tuning of the EDC build model based at least in part on said analyzing the EDC build predictions produced from the protocol documents of the testing dataset.

18. A non-transitory computer-readable medium storing instructions that, when executed by one or more processors of a computer, cause said one or more processors to perform a method for building an electronic data capture (EDC) system, the method comprising:
forming a training dataset from a set of clinical trial protocol documents and corresponding EDC builds, each EDC build comprising a machine-readable specification file defining electronic case report form (eCRF) data fields, edit checks for validating data entered into the eCRF data fields, and folder structures for storing study data within the EDC system;
using the set of clinical trial protocol documents and corresponding EDC builds of the training dataset to tune a pre-trained language model to produce an EDC build model;
inputting a clinical trial protocol document to the EDC build model to produce an EDC build prediction comprising a corresponding machine-readable specification file; and
generating data structures of the EDC system based at least in part on the EDC build prediction by loading the machine-readable specification file into an EDC system platform to instantiate the eCRF data fields, the edit checks for validating the data entered into the eCRF data fields, and the folder structures for storing study data within the EDC system.

19. The computer-readable medium of claim 18, wherein said generating data structures of the EDC system comprises generating one or more electronic case report forms.

20. The computer-readable medium of claim 18, wherein said generating data structures of the EDC system comprises generating one or more folder structures for managing EDC system information.

21. The computer-readable medium of claim 18, wherein the EDC build prediction is in the form of an extensible markup language (XML) document.

22. The computer-readable medium of claim 18, wherein said forming the training dataset comprises dividing the set of protocol documents and corresponding EDC builds into the training dataset and a testing dataset.

23. The computer-readable medium of claim 22, further comprising:

inputting the protocol documents of the testing dataset to the EDC build model to produce EDC build predictions; and analyzing the EDC build predictions produced from the protocol documents of the testing dataset to determine accuracy of the EDC build model.

24. The computer-readable medium of claim 23, further comprising performing tuning of the EDC build model based at least in part on said analyzing the EDC build predictions produced from the protocol documents of the testing dataset.

* * * * *